US005693329A

United States Patent [19]
Marchi-Lemann et al.

[11] Patent Number: 5,693,329
[45] Date of Patent: Dec. 2, 1997

[54] COSMETIC COMPOSITION WHICH PREVENTS OR ATTENUATES THE PHOTO-REACTIVITY OF TITANIUM DIOXIDE NANOPIGMENTS

[75] Inventors: Patricia Marchi-Lemann; Christian Colin, both of Paris, France

[73] Assignee: L'Oreal, Paris, France

[21] Appl. No.: 527,429

[22] Filed: Sep. 13, 1995

[30] Foreign Application Priority Data

Sep. 13, 1994 [FR] France ................................. 94 10924

[51] Int. Cl.$^6$ ................. A61K 7/021; A61K 9/107; A61K 9/14
[52] U.S. Cl. ................. 424/401; 424/59; 424/63; 424/490; 514/844; 514/938; 514/952; 514/970
[58] Field of Search ................................. 424/489, 490, 424/401, 59, 63

[56] References Cited

U.S. PATENT DOCUMENTS

| | | | |
|---|---|---|---|
| 3,847,640 | 11/1974 | Daubenspeck et al. | 106/300 |
| 5,456,749 | 10/1995 | Iwasa et al. | 106/417 |

*Primary Examiner*—Thurman K. Page
*Assistant Examiner*—James M. Spear
*Attorney, Agent, or Firm*—Cushman Darby & Cushman IP Group of Pillsbury Madison & Sutro LLP

[57] ABSTRACT

Cosmetic composition, characterized in that it contains titanium dioxide nanopigments coated with at least aluminium derivatives in a cosmetically acceptable, fairly non-polar medium having a conductivity of less than 100 µSiemens and containing at least one fatty phase.

27 Claims, No Drawings

COSMETIC COMPOSITION WHICH PREVENTS OR ATTENUATES THE PHOTO-REACTIVITY OF TITANIUM DIOXIDE NANOPIGMENTS

The present invention relates to cosmetic compositions containing titanium oxide nanopigments, these compositions having the advantage of being particularly stable to sunlight.

Titanium dioxide in the form of nanopigments is well known for its property of absorbing light, in particular in the UV range. For this reason, it is used in cosmetic compositions as an inorganic screening agent, as a replacement for or in combination with organic screening agents.

However, UV absorption generates undesirable phenomena of oxidation-reduction of the titanium oxide, which are manifested by a change in colour of the composition. Indeed, a blueing or a yellowing and an oxidation of the other components are observed.

Without this explanation being limiting, it is thought that light catalyses the reduction of titanium IV (white) into titanium III (blue). These reactions possibly take place even at a very low percentage of titanium oxide.

Consequently, means are sought for protecting such compositions in order especially to avoid these problems of oxidation and of change in colour, which are undesirable in the cosmetics field.

However, titanium dioxide, which is used as the agent for protection against ultraviolet radiation, must continue to play its protective rôe.

The use of titanium oxide nanopigments in sun compositions in combination with sunscreens has already been described in the prior art, in particular in U.S. Pat. No. 5,028,417 or, in isolation, JP-A-0,038,436.

The problem of the photo-reactivity of titanium oxide has also been raised, and patent GB-A-2,217,987 proposes the use of nanopigments coated with an aluminium derivative for the purpose of minimizing the reduction photoinduced by titanium dioxide.

Patent JP-03115211 proposes a surface treatment using salts of silica and alumina, which would allow for better dispersibility of the nanopigments and an attenuation of the denaturation of the surrounding oils.

Finally, PCT WO 9009777 considers the addition of phosphate salts, either by surface treatment of the pigments or by simple introduction into the formula in order to reduce the photocatalysis.

The objective pursued by these various solutions recommended in the prior art consists essentially in treating titanium dioxide so as to render it inert with respect to light. It has, however, been observed that such treatments are not always sufficient. It has therefore also been considered to use antioxidants in the presence of titanium dioxide nanopigments.

The inventors have discovered that by using $TiO_2$ nanopigments protected by a surface treatment consisting of salts of aluminium and of silicon in a fairly nonpolar medium, it was possible to obtain compositions based on titanium dioxide which are particularly stable to UV radiation and which do not cause oxidation of the other components present in the composition.

The subject of the invention is thus a novel cosmetic composition based on titanium dioxide nanopigments.

Another subject of the invention consists of the cosmetic treatment process using such compositions.

The subject of the invention is also a process for preventing or attenuating the photo-reactivity of titanium dioxide nanopigments.

Other subjects of the invention will emerge on reading the description and the examples which follow.

The cosmetic composition in accordance with the invention is essentially characterized in that it contains titanium dioxide nanopigments protected by a surface treatment with at least one aluminium derivative in a cosmetically acceptable, fairly nonpolar medium having a conductivity of less than 100 μSiemens and containing at least one fatty phase.

A surface treatment with derivatives of aluminium and of silicon is preferably used.

The derivatives of aluminium and of silicon are more particularly chosen from aluminium oxide and silicon oxide. Their proportion is such that the total percentage of aluminium and of silicon present in the coating represents at least 5% by weight relative to the weight of titanium dioxide. The amount of aluminium is preferably greater than the amount of silicon. The content of coating is preferably between 5 and 30% by weight relative to the weight of titanium dioxide, and in particular between 5 and 20%.

A mixture of aluminium oxide and silicon oxide is preferably used. The $Al_2O_3/SiO_2$ ratio is preferably greater than or equal to 3 and less than or equal to 8, $Al_2O_3$ being present in a greater amount relative to the amount of $SiO_2$, which is used in an amount greater than or equal to 1% by weight relative to the weight of titanium dioxide.

The nanopigments of titanium dioxide protected by a surface treatment with at least one aluminium derivative and preferably with derivatives of aluminium and of silicon may, in one embodiment of the invention, form the subject of an additional surface coating such as by silicones, amino acids, fatty acid salts other than aluminium salts, lecithin, etc.

Such an additional coating makes it especially possible to facilitate dispersion of the titanium dioxide in the medium.

The cosmetically acceptable medium is fairly nonpolar; it has a conductivity of less than 100 μSiemens measured using an M90 CHECKMATE multiparameter from the company Mettler-Toledo.

The cosmetically acceptable medium containing at least one fatty phase, which is used in accordance with the invention, may be anhydrous or hydrated and, in the latter case, is in the form of a water-in-oil (W/O) or oil-in-water (O/W) emulsion.

This fatty phase consists of an oil or a mixture of oils or fats.

The oils or mixtures of oils or fats should be fairly nonpolar or entirely nonpolar. Preferably, the dielectric constant of the oil or of the mixtures used should be less than 3 and preferably less than 2.5.

The polarity index is preferably greater than 24 mN/m and in particular greater than 35 mN/m.

In the case of mixtures of oils, it is possible to use a more polar oil in the mixture, on condition that the final mixture is fairly nonpolar, as defined above.

Fairly nonpolar oils of carbon-based type are generally used. Hydrocarbons such as liquid petrolatum, squalane, short triglycerides and esters, that is to say esters containing 1 to 6 carbon atoms in the alkyl radical, such as isopropyl adipate, isopropyl myristate, isopropyl palmitate or alternatively a benzoate of $C_{12}$–$C_{15}$ alcohols, may be mentioned. Oils such as octyldodecanol or myristyl alcohol oxypropylenated with 1 to 5 mol of propylene oxide may also be used.

The compositions in accordance with the invention preferably contain between 0.5 and 30%, and preferably from 0.5 to 10%, by weight of titanium dioxide, having a particle size less than or equal to 200 nm and preferably less than 100 nm, coated with derivatives of aluminium and of silicon. The cosmetically acceptable, fairly nonpolar fatty phase is generally present in proportions of 5 to 99.5% by weight relative to the total weight of the composition. These proportions are preferably between 5 and 50% for the emulsions.

The compositions in accordance with the invention may also contain salts such as NaCl and $MgSO_4$. These salts should, however, be used in proportions such that they do not increase the conductivity of the medium to a value of greater than 100 μSiemens.

These compositions may also contain antioxidants such as extract of sesame oil, superoxide dismutase, caffeine, cytochrome C, tert-butylhydroxytoluene, diethylenetriaminepentaacetic acid, ethoxyquine, lactoperoxidase and dehydroxyascorbic acid, ethoxyquine being particularly preferred.

The Applicant has observed that the compositions were particularly stable when they contain, in addition to the titanium dioxide nanopigments containing a surface coating consisting of derivatives of aluminium and of silicon in a fairly nonpolar medium, ethoxyquine as antioxidant.

The proportions of antioxidants are generally between 0.01 and 2% and preferably between 0.01 and 0.05%.

These compositions are generally prepared by introducing the nanopigments into the fatty phase of the composition, thereby allowing better dispersion of the pigments given the higher shear forces employed in the more viscous media.

These compositions may also contain other adjuvants usually used in cosmetics, with the proviso that they do not increase the conductivity of the composition to a value of greater than 100 μSiemens. They may be in the form of an emulsion, a cream or an optionally thickened oil. These compositions may be packaged as an aerosol and may be in the form of a foam.

The subject of the invention is also a process for preventing or attenuating the photo-reactivity of titanium dioxide nanopigments in cosmetic compositions. This process is essentially characterized in that the titanium dioxide nanopigments are coated with a derivative of aluminium and of silicon as defined above and in that these coated nanopigments are introduced into a cosmetically acceptable, fairly nonpolar medium having a conductivity of less than 100 μSiemens. This medium preferably comprises a fatty phase and has the characteristics as defined above.

Another subject of the invention consists of the cosmetic treatment process consisting in applying to the skin a composition as defined above. This composition may be used for protection against the sun and as a make-up product, such as a foundation, a mascara, etc.

The examples which follow are intended to illustrate the invention without, however, being limiting in nature.

EXAMPLE 1

The following composition is prepared:

| | | |
|---|---|---|
| Fatty phase | Cetylstearyl alcohol and oxyethylenated cetylstearl alcohol | 7% |
| | Glyceryl distearate and glyceryl stearate | 2% |
| | Cetyl alcohol | 1.5% |
| | Polydimethylsiloxane | 1.5% |
| | Butyl p-hydroxybenzoate | 0.2% |
| | Liquid petrolatum | 15% |
| Aqueous phase | Glycerol | 20% |
| | Water | 45.6% |
| | Imidazolindiylurea | 0.2% |

-continued

| | | |
|---|---|---|
| Preserving agents | Water | 2% |
| Pigment | MT 100T* | 5% |

The conductivity of the medium is 30 μSiemens.

*MT 100T is a titanium nanodioxide (rutile treated with aluminium stearate (80/20) having a mean particle size of 15 nm), sold by the company Tayca.

Procedure:

The pigments are incorporated into the fatty phase (heated to about 80° C.) with stirring using a Moritz stirrer.

This phase is then introduced into the aqueous phase (80° C.) with stirring using a Moritz stirrer.

This stirring is continued for 5 minutes and, when the emulsion has reached about 40° C., the preserving agents are then added.

The stirring is stopped when the emulsion is at room temperature. Stirring to the paste may then be completed.

EXAMPLE 2

The following composition is prepared:

| | | |
|---|---|---|
| Fatty phase | Cetylstearyl alcohol and oxyethylenated cetylstearl alcohol | 5% |
| | Glyceryl distearate and glyceryl stearate | 1% |
| | Cetyl alcohol | 1% |
| | Oil (various oils were used, according to Table I) | 6% |
| | Vitamin F* | 6% |
| Pigment | MT 100T | 100 |
| Aqueous phase | Water qs 100 | 45.6% |

This composition is prepared as described in Example 1.

*Vitamine F: cis,cis-9,12-liinoleic acid (50%) with the presence of oleic acid (5%) and stabilized 9,11-octadecadienoic acid (40%).

TABLE I which follows demonstrates the importance of the fairly nonpolar medium, the polar jojoba oil having a negative effect on the stability of vitamin F, in the presence of the pigment.

ΔE expresses the difference in colour between the sample at time 0 (before exposure) and after exposure.

It is determined by the formula $\Delta E = \sqrt{\Delta L^2 + \Delta a^2 + \Delta b^2}$, in which the parameter L defines the lighter or darker nature, a: the blue or green hue, b: the yellow or red hue, or Lab system.

TABLE I

CHANGE OF VITAMIN F IN THE PRESENCE OF VARIOUS OILS

| | Percentage of activation (+) or of inhibition (−) of the oxidation of vitamin F after various treatments | | ΔE BLUEING | |
|---|---|---|---|---|
| Compositions tested | 1 h uVA + 5 d 37° | 24 h UVA | After 1 h UVA | After 24 h UVA |
| 1 Liquid petrolatum + MT100T | −67% | −63% | 2.99 | 13.96 |
| 2 Finsolv LIN + MT100T | −54% | nd | 11.65 | nd |

TABLE I-continued

CHANGE OF VITAMIN F IN THE PRESENCE OF VARIOUS OILS

| Compositions tested | Percentage of activation (+) or of inhibition (−) of the oxidation of vitamin F after various treatments | | ΔE BLUEING | |
|---|---|---|---|---|
| | 1 h uVA + 5 d 37° | 24 h UVA | After 1 h UVA | After 24 h UVA |
| 3 Eutanol G + MT100T | −63% | nd | 8.99 | nd |
| 4 Jojoba + MT100T* | +46% | +99% | 8.51 | 19.1 |
| 5 Witconol APM + MT100T | −62% | nd | 5.74 | nd |

*polar oil - comparative

| | |
|---|---|
| FINSOLV | is a benzoate of $C_{12}-C_{15}$ alcohols sold by the company Finetex. |
| EUTANOL G | is octyldodecanol, sold by the company Henkel. |
| WITCONOL APM | is myristyl alcohol oxypropylenated with 3 mol of propylene oxide, sold by the company Witco. |

EXAMPLE 3

The following composition is prepared:

| | |
|---|---|
| Cetostearyl alcohol and cetosteareth | 5% |
| Glyceryl distearate and glyceryl stearate | 1% |
| Cetyl alcohol | 1% |
| Jojoba oil | 6% |
| Vitamin F | 6% |
| Pigment (various pigments were used, according to Table II) 3a to 3c | 5% |
| Water qs | 100 |

This preparation is made according to the scheme described in Example 1.

TABLE II

CHANGE OF VITAMIN F IN THE PRESENCE OF VARIOUS PIGMENTS

| Compositions tested | Percentage of activation (+) or of inhibition (−) of the oxidation of vitamin F after various treatments (Expressed relative to the pigment-free base) | | ΔE BLUEING | |
|---|---|---|---|---|
| | 1 h UVA | 24 h UVA | After 1 h UVA | After 6 h UVA |
| 3a MT 100T | +1758% | −44% | 10.31 | 12.46 |
| 3b M 262 | +731% | −23% | 3 | 8 |
| 3c* P 25 | '5652% | +119% | 21.24 | 21.65 |

*not in accordance with the invention

TABLE II shows the change in the composition in accordance with Example 3 using various pigments.

It is observed that the nanopigment P25, which is a titanium nanodioxide having a particle size of 20 nm, marketed by the company Degussa and which bears no coating of aluminium and silicon, is very reactive. The use of coated nanopigment such as the product MT100T, which is a titanium nanooxide (rutile treated with aluminium stearate 80/20) having a particle size of 15 nm, sold by the company Tayca or the product named UV-Titan M262, which is a titanium nanooxide (anatase treated with alumina, silica 6.3/1) of particle size 20 nm with a 2% coating content of PDMS, marketed by the company Kemira.

EXAMPLE 4

These compositions are prepared from the composition of Example 3 containing the product MT 100T as pigment, with introduction of an antioxidant.

TABLE III

| Example 3 with MT 100T | QSP-100 | QSP-100 |
|---|---|---|
| Dehydroascorbic acid | 1% | — |
| Ethoxyquine | — | 1% |
| Blueing after 1 hour UVA | 3.35 | 1.95 |
| % of activation or inhibiton of the oxidatin of vitamin F as a % relative to Example 3 with MT 100T: | | |
| 1 h UVA | −100% | −100% |
| 1 h UVA + 5 days at 37° C. | −93% | −100% |

EXAMPLE 5

The example which follows is intended to illustrate the use of the invention with mixtures of more or less polar oils. This example is based on the composition of Example 2. TABLE IV illustrates the results obtained.

TABLE IV

| Mixture of two oils of different polarities in the vitamin F emulsion containing 5% MT 100T | | | |
|---|---|---|---|
| Mixture of oils | Liquid petrolatum (fairly nonpolar) | 4.5% | 1.5% |
| (% weight in the formula) | Benxyl ester (polar) | 1.5% | 4.5% |
| Blueing (ΔE) after 1 hour of exposure to the SUNTEST | | 3 | 4 |

We claim:

1. Cosmetic composition, characterized in that it contains titanium dioxide nanopigments coated with at least one aluminum oxide in a cosmetically acceptable, fairly nonpolar medium having a conductivity of less than 100 μ Siemens and containing at least one fatty phase.

2. Composition according to claim 1, characterized in that the titanium dioxide nanopigments are coated with oxides of aluminum and of silicon.

3. Composition according to claim 2, characterized in that the nanopigment is coated with a mixture of aluminum oxide and silicon oxide, the aluminum and the silicon constituting at least 5% by weight relative to the weight of titanium dioxide, and the amount of aluminum is greater than the amount of silicon.

4. Composition according to claim 1, characterized in that the content of coating in the nanopigment is between 5 and 30% by weight relative to the weight of the titanium dioxide.

5. Composition according to claim 2, characterized in that the $Al_2O_3/SiO_2$ ratio is greater than or equal to 3 and less than or equal to 8, $Al_2O_3$ being present in an amount greater than the amount of $SiO_2$, which is present in an amount equal to or greater than 1% by weight relative to the weight of the titanium dioxide.

6. Composition according to claim 1, characterized in that the titanium dioxide contains an additional coating which facilitates dispersion of the pigment in the medium.

7. Composition according to claim 6, characterized in that the additional coating consists of silicones, amino acids, fatty acid salts other than the aluminum salts, and lecithin.

8. Composition according to claim 1, characterized in that the cosmetically acceptable medium containing at least one fatty phase is anhydrous or is in the form of a water-in-oil or oil-in-water emulsion.

9. Composition according to claim 1, characterized in that the fatty phase consists of an oil or a mixture of oils or fats which is fairly nonpolar or entirely nonpolar.

10. Composition according to claim 9, characterized in that the dielectric constant of the oil or of the mixture of oils or fats is less than 3.

11. Composition according to claim 9, characterized in that the polarity index of the oil or of the mixture of oils or fats is greater than 24 mN/m.

12. Composition according to claim 1, characterized in that the fat is an oil chosen from hydrocarbons or short triglycerides and esters, or a mixture of these oils.

13. Composition according to claim 1, characterized in that the coated nanopigments are present in proportions between 0.5 and 30% by weight relative to the total weight of the composition.

14. Composition according to claim 1, characterized in that the coated titanium dioxide nanopigments have a particle size less than or equal to 200 nm.

15. Composition according to claim 1, characterized in that the fairly nonpolar fatty phase constitutes 5 to 99.5% by weight relative to the total weight of the composition.

16. Composition according to claim 1, characterized in that it contains salts in proportions such that the conductivity of the medium remains below 100 µSiemens.

17. Composition according to claim 1, characterized in that the composition contains antioxidants.

18. Composition according to claim 1, characterized in that the antioxidants are chosen from extract of sesame oil, superoxide dismutase, caffeine, cytochrome C, tert-butylhydroxytoluene, diethylenetriaminepentaacetic acid, ethoxyquine, lactoperoxidase and dehydroxyascorbic acid.

19. Composition according to claim 1, characterized in that the antioxidant is ethoxyquine.

20. Composition according to claim 1, characterized in that the antioxidant is used in proportions between 0.01 and 2% by weight.

21. Process for the preparation of a composition as defined in claim 1, characterized in that the coated nanopigments are introduced into the fatty phase of the composition, this fatty phase then being introduced optionally, into the aqueous phase.

22. Process for preventing or attenuating the photoreactivity of titanium dioxide nanopigments in cosmetic compositions, characterized in that the titanium dioxide nanopigments are coated with at least one aluminum oxide and in that the titanium dioxide thus coated is introduced into a cosmetically acceptable, fairly nonpolar medium having a conductivity of less than 100 µSiemens.

23. Process according to claim 22, characterized in that the cosmetically acceptable medium contains at least one fatty phase which is anhydrous or is in the form of a water-in-oil or oil-in-water emulsion.

24. Cosmetic treatment process for the skin, characterized in that a composition as defined in claim 1 is applied to the skin.

25. Composition according to claim 1, wherein the content of coating in the nanopigment is between 5 and 20% by weight relative to the weight of the titanium dioxide.

26. Composition according to claim 1, wherein the coated titanium dioxide nanopigments have a particle size less than or equal to 100 nm.

27. Composition according to claim 17, wherein the antioxidant is used in proportions between 0.01 and 0.05% by weight.

* * * * *